United States Patent
Bass et al.

(10) Patent No.: US 9,127,202 B1
(45) Date of Patent: Sep. 8, 2015

(54) BIOCOMPATIBLE NANO RARE EARTH OXIDE UPCONVERTERS FOR IMAGING AND THERAPEUTICS

(75) Inventors: Michael Bass, Indian River Shores, FL (US); Sudipta Seal, Orlando, FL (US); William T. Self, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 697 days.

(21) Appl. No.: 12/505,023

(22) Filed: Jul. 17, 2009

Related U.S. Application Data (60) Provisional application No. 61/081,903, filed on Jul. 18, 2008.

(51) Int. Cl.
| | | |
|---|---|---|
| *C09K 11/77* | (2006.01) | |
| *C09K 11/08* | (2006.01) | |
| *B82Y 5/00* | (2011.01) | |

(52) U.S. Cl.
CPC ......... *C09K 11/7715* (2013.01); *C09K 11/7766* (2013.01); *B82Y 5/00* (2013.01); *C01P 2004/64* (2013.01)

(58) Field of Classification Search
CPC ............... C09K 11/00; C09K 11/7702; C09K 11/7715; C09K 11/7728; C09K 11/7766; C09K 11/7769; C09K 11/7783; C09K 11/08; C09K 11/7716; C09K 11/7767; C09K 11/7784; Y10S 977/773; Y10S 977/775; Y10S 977/776; Y10S 977/779; A61K 2800/412; A61K 2800/413; A61K 2800/434; A61K 6/0008; A61K 6/025; C01P 2004/60; C01P 2004/62; C01P 2004/64; B82Y 20/00; B82Y 5/00; B82Y 15/00; B82Y 30/00; H01L 33/502; Y02B 20/181; C04B 2235/3224
USPC ..... 252/301.4 R, 301.4 H; 424/489, 490, 9.3, 424/401; 313/463, 467, 468, 486, 501, 503; 977/773, 775, 778, 904, 906, 776; 428/402, 489, 490, 690
See application file for complete search history.

(56) References Cited

U.S. PATENT DOCUMENTS

| | | | |
|---|---|---|---|
| 5,089,860 A | 2/1992 | Deppe et al. | |
| 5,411,647 A | 5/1995 | Johnson et al. | |
| 5,486,359 A | 1/1996 | Caplan et al. | |
| 5,910,311 A | 6/1999 | Boussouira et al. | |
| 5,961,993 A | 10/1999 | Boussouira et al. | |
| 6,042,714 A | 3/2000 | Lin et al. | |
| 6,103,247 A | 8/2000 | Boussouira et al. | |
| 6,139,985 A | 10/2000 | Borglum et al. | |
| 6,265,825 B1 * | 7/2001 | Asano ........................... 313/582 |
| 6,316,012 B1 | 11/2001 | N'Guyen et al. | |
| 6,327,074 B1 | 12/2001 | Bass et al. | |
| 6,342,322 B1 * | 1/2002 | Kakinuma et al. ............. 430/17 |
| 6,368,577 B1 | 4/2002 | Kropf et al. | |
| 6,406,685 B1 | 6/2002 | Philippe et al. | |
| 6,468,551 B1 | 10/2002 | Diec et al. | |
| 6,497,863 B1 | 12/2002 | Wachter | |
| 6,497,875 B1 | 12/2002 | Sorrell et al. | |
| 6,501,590 B2 | 12/2002 | Bass et al. | |
| 6,592,746 B1 | 7/2003 | Schmid-Schoenbein et al. | |
| 6,654,161 B2 | 11/2003 | Bass et al. | |
| 6,844,387 B2 | 1/2005 | Bass et al. | |
| 6,890,896 B1 | 5/2005 | Shashoua | |
| 7,005,504 B2 | 2/2006 | Hsei et al. | |
| 7,075,707 B1 * | 7/2006 | Rapaport et al. ............... 359/326 |
| 7,141,227 B2 | 11/2006 | Chan | |
| 7,270,813 B2 | 9/2007 | Shimp et al. | |
| 7,347,987 B2 | 3/2008 | McGinnis et al. | |
| 7,431,758 B2 | 10/2008 | Ota et al. | |
| 7,442,686 B2 | 10/2008 | Lasko et al. | |
| 7,471,706 B2 | 12/2008 | Bass et al. | |
| 7,504,356 B1 | 3/2009 | Self et al. | |
| 7,507,480 B2 | 3/2009 | Sugama | |
| 7,534,453 B1 | 5/2009 | Rzigalinski et al. | |
| 7,563,459 B2 | 7/2009 | Phillips | |
| 7,642,250 B2 | 1/2010 | Williams | |
| 7,687,505 B2 | 3/2010 | Sugaya et al. | |
| 7,725,802 B2 | 5/2010 | Eroz et al. | |
| 7,772,375 B2 | 8/2010 | Greferath et al. | |

(Continued)

FOREIGN PATENT DOCUMENTS

| | | | |
|---|---|---|---|
| KR | 1020030005760 A1 * | 6/2004 | |
| WO | WO 99/15891 | 4/1999 | |

(Continued)

OTHER PUBLICATIONS

Xijuan et al, 'Size-dependent optical properties of nanocrystalline CeO2:Er obtained by combustion synthesis', Sep. 24, 2001, Phys. Chem. Chem. Phys., vol. 3, pp. 5266-5269.*

Guo, 'Green and red upconversion luminescence in CeO2:Er3+ powders produced by 785 nm laser', Oct. 10, 2006, Journal of Solid State Chemistry 180, p. 127.*

Guo, 'Green and red upconversion luminescence in CeO2:ER3+ powders produced by 785 nm laser', available online Oct. 10, 2006, Journal of Solid State Chemistry, vol. 180, pp. 127-131.*

Machine translation of KR1020030005760A1.*

(Continued)

*Primary Examiner* — Matthew E Hoban
*Assistant Examiner* — Lynne Edmondson
(74) *Attorney, Agent, or Firm* — William Greener; Alek Szecsy; Bond, Schoeneck & King, PLLC (57) ABSTRACT

Methods and systems biomedical application of up conversion nanoparticles. Co-doped cerium oxide nanoparticles were synthesized by precipitation technique. Up conversion nano cerias are biocompatible as a biomarker with antioxidant properties. Up conversion nano cerias interact in a cell specific manner showing catalase mimetic activity. With suitable surface targeting ligands, up conversion nano cerias can be used for site selective drug delivery for the treatment of diseases like cancer.

10 Claims, 7 Drawing Sheets

(56) References Cited

U.S. PATENT DOCUMENTS

| | | | |
|---|---|---|---|
| 7,888,119 B2 | 2/2011 | Sugaya et al. | |
| 7,899,093 B1 * | 3/2011 | Bass et al. | 372/21 |
| 7,906,147 B2 | 3/2011 | Hainfeld et al. | |
| 7,924,617 B2 | 4/2011 | Yip | |
| 8,080,420 B2 | 12/2011 | Sugaya et al. | |
| 8,097,270 B2 | 1/2012 | Ketelson et al. | |
| 8,172,901 B2 | 5/2012 | Altman et al. | |
| 2002/0020830 A1 * | 2/2002 | Bass et al. | 252/301.16 |
| 2003/0050709 A1 | 3/2003 | Noth et al. | |
| 2003/0187077 A1 | 10/2003 | Chane-Ching | |
| 2004/0062753 A1 | 4/2004 | Rezania et al. | |
| 2005/0112389 A1 * | 5/2005 | Loureiro et al. | 428/472 |
| 2005/0159820 A1 | 7/2005 | Yoshikawa et al. | |
| 2005/0164377 A1 | 7/2005 | Miyabayashi et al. | |
| 2005/0171192 A1 | 8/2005 | Gehlsen | |
| 2006/0110440 A1 | 5/2006 | Sugaya et al. | |
| 2006/0141137 A1 * | 6/2006 | Anderson et al. | 427/115 |
| 2006/0280729 A1 | 12/2006 | Mistry | |
| 2007/0003621 A1 | 1/2007 | Nangia et al. | |
| 2009/0087493 A1 | 4/2009 | Dai et al. | |
| 2009/0098574 A1 | 4/2009 | Brisson et al. | |
| 2010/0151000 A1 | 6/2010 | Thomas et al. | |

FOREIGN PATENT DOCUMENTS

| | | |
|---|---|---|
| WO | WO 03/059263 A2 | 7/2003 |
| WO | WO 2006/118954 A2 | 11/2006 |
| WO | WO 2007/002662 A2 | 1/2007 |
| WO | WO 2008/064357 A2 | 5/2008 |
| WO | PCT/US2009/041675 | 10/2009 |
| WO | WO 2009/132277 A1 | 10/2009 |

OTHER PUBLICATIONS

Zhang et al., "Preparation and Optical Properties of Nanosized CeO2:Er,Yb", Oct. 2000, Proceedings of ICETS 2000-ISAM, pp. 695-698.*
PCT/US2011/0044329, PCT International Search Report and the Written Opinion of the International Searching Authority, cover page.
Buettner, et al., Ascorbate (Vitamin C) its antioxidant chemistry, Free Radical and Radiation Biology Program, Dept. of Radiation Oncology, University of Iowa, 1 page.
Rzigalinski, et al. Cerium oxide nanoparticles increase the lifespan of cultured brain cells and protect against free radical and mechanical trauma, FASEB Journal, 2003, pp. A606, vol. 17, No. 4-5, Abstract No. 377.24.
Niu, et al., Cardioprotective effects of cerium oxide nanoparticles in a transgenic murine model of cardiomyopathy, Cardiovas. Res., 2006, pp. 549-559, vol. 73, No. 3.
Qureshi, et al. Increased exhaled nitric oxide following autologous peripheral hematopoietic stem-cell transplantation: a potential marker of idopathic pneumonia syndrome, Chest, 2004, pp. 281-287, vol. 125, No. 1.
Ohgushi, et al., Stem cell technology and bioceramics: from cell to gene engineering, J. Biomed. Mat. Res., 1999, pp. 913-927, vol. 48, abstract.
Dal Maschio, et al., Influence of Ce+/Ce4+ ratio on phase stability and residual stress field in ceria-yttria stabilized zirconia plasma-sprayed coatings, J. Mat. Sci., 1992, pp. 5591-5596, vol. 27, abstract.
Ramsfjell, et al., Distinct requirements for optimal growth and in vitro expansion of human CD34+ CD38− bone marrow long-term culture-initiating cells (LTC-IC), extended LTC-IC, and murine in vivo long-term reconstituting stem cells, Blood, 1999, pp. 4093-4102, vol. 99, No. 12, abstract.
Devasenpathi, et al., Forming near net shape free-standing components by plasma spraying, Mat. Let., 2002, pp. 882-886, vol. 57.
Imamura, et al., Drusen, choroidal neovascularization, and retinal pigment epithelium dysfunction in SOD1-deficient mice: a model of age-related macular degeneration, PNAS, 2006, pp. 11282-11287, vol. 103, No. 30.
Hollyfield, et al., Oxidative damage-induced inflammation initiates age-related macular degeneration, Nature Medicine, 2008, pp. 194-198, vol. 14.
Birch, et al., Age-related macular degeneration: a target for nanotechnology derived medicines, International Journal of Nanomedicine, 2007, pp. 65-77, vol. 2, No. 1.
Maulik, N., Reactive oxygen species drives myocardial angiogenesis?, Antioxidants & Redox Signaling, 2006, pp. 2161-2168, vol. 8, Nos. 11-12.
McGinnis, et al. U.S. Appl. No. 12/772,523 Office Action mailed Sep. 15, 2011.
Ohia, et al., Pharmacological consequences of oxidative stress in ocular tissues, Mutation Research, 2005, pp. 22-36, vol. 579.
Liu, et al. Subtype lesions of neovascular age-related macular degeneration in Chinese patients, Graefe's Arch Clin Exp Opthalmol, 2007, pp. 1441-1445, vol. 245.
Silva, Seeing the benefits of ceria, Nature Nanotechnology, 2006, pp. 92-94, vol. 1.
Hahn, et al., Maculas affected by age-related macular degeneration contain increased chelatable iron in the retinal pigment epithelium and Bruch's membrane, Arch. Opthalmol., 2003, pp. 1099-1105, vol. 121.
Haywood, et al., Inflammation and angiogenesis in osteoarthritis, Arthritis & Rheumatism, 2003, pp. 2173-2177, vol. 48, No. 8.
Chen, et al., Rare earth nanoparticles prevent retinal degeneration induced by intracellular peroxides, Nature Nano Technology, 2006, pp. 142-148, vol. 1, No. 2, abstract.
Moongkarndi, et al., Antiproliferation, antioxidation and induction of apoptosis by *Garcinia mangostana* (mangosteen) on SKBR3 human brest cancer cell line, J. of Ethno-Pharmacology, 2004, pp. 161-166, vol. 90, abstract.
Margrain, et al., Do blue light filters confer protection against age-related macular degeneration?, Progess in Retinal and Eye Research, 2004, pp. 523-531, vol. 23, abstract.
Bailey, et al., Cerium oxide nanoparticles extend cell longevity and act as free radical scavengers, online, retrieved on Apr. 24, 2006, retrieved from http://www.med.miami.edu/mnbws/Rzigalinski11.html, abstract.
Tsai, The study of the synthesis of nano-grade cerium oxide powder, Materials Letters, 2004, pp. 2270-2274, vol. 58, abstract.
Rzigalinski, et al., Cerium oxide nanoparticles increase the lifespan of cultured brain cells and protect against free radical and mechanical trauma, FASEB Journal, 2003, vol. 17, No. 4-5, page abstract No. 377.24, abstract.
Cook, et al., Neuronal damage induced by polychlorinated biphenyls is partially reversed by cerium oxide nanoparticles, online, 2003, retrieved from http://sfn.scholarone.com/itin2003/main.htm]?new_page_id=126&abstract_id=14513&p_num=669.13&is_tech=0>, retrieved on Aug. 8, 2008, abstract.
Tusnekawa, S., et al., Lattice relaxation of monosize CeO2−x nanocrystalline particles, Applied Surface Science Elsevier Netherlands, 1999, pp. 53-56, vol. 152, No. 1-2, abstract.
Hooper, et al., New treatment in age-related macular degeneration, Clinical & Experimental Opthalmology, 2003, pp. 376-391, vol. 31, abstract.
Suzuki, et al., Preparation and characteristics of magnetite-labelled antibody with the use of poly(ethylene glycol) derviatives, Biotech. and Applied Biochem., 1995, pp. 335-345, vol. 21.
Dong, et al., Activation of glassy carbon electrodes by dispersed metal oxide particles, Dept. of Chemistry, OSU, downloaded 2011, pp. 813, abstract.
Shui, et al., Morphological observation on cell death and phagocytosis induced by ultraviolet irradiation inb a cultured human lens epithelial cell line, Exp. Eye Res., 2000, pp. 608-619, vol. 71, No. 6, abstract.
Xijuan, et al., Size-dependent optical properties of nanocrystalline CeO2:Er obtained by combustion synthesis, Phys. Chem., 2001, pp. 5266-5269, vol. 3, abstract.
Guo, Green and red upconversion luminescence in CeO2:Er3+ powders produced by 785 nm laser, Journal of Solid State Chemistry, 2007, pp. 127-131, vol. 180, No. 1, abstract.

(56) References Cited

OTHER PUBLICATIONS

Perez, et al., Synthesis of biocompatible dextran-coated nanoceria with pH-Dependent antioxidant properties, Small, 2008, pp. 552-556, vol. 4, No. 5, abstract.

Pirmohamed, et al., Nanoceria exhibit redox state-dependent catalase mimetic activity, Chem. Comm, 2010, pp. 2736-2738, vol. 46, abstract.

Chen, et al., Rare earth nanoparticles prevent retinal degeneration induced by intracellular peroxides, Nature Publishing Group, 2006, pp. 1-9, abstract.

Karakoti, et al., Direct synthesis of nanoceria in aqueous polyhydroxyl solutions, J. Phys. Chem. C, 2007, pp. 17232-17240, vol. 111, No. 46, abstract.

Tarnuzzer, et al., Vacancy engineered ceria nanostructures for protection from radiation-induced cellular damage, Nano Lett, 2005, pp. 2573-2577, vol. 4, No. 12, abstract.

Heckert, et al., The role of cerium redox state in the SOD mimetic of nanoceria, Biomaterials, 2008, pp. 2705-2709, vol. 29, abstract.

Schubert, et al., Cerium and yttrium oxide nanoparticles are neuroprotective, Biochemical and Biophysical Research Communications, 2006, pp. 86-91, vol. 342.

Zhang, et al., Cerium oxide nanoparticles: size selective formation and structure analysis, Applied Physics Leters, 2002, pp. 127-129, vol. 81, No. 1.

Patil, et al., Surface-derived nanoceria with human carbonic anhydrase II inhibitors and flourphores: a potential drug delivery device, J. Phys. Chem. C., 2007, pp. 8437-8442, vol. 111, No. 24, abstract.

Patil, et al., Synthesis of nanocrystalline ceria particles for high temperature oxidation resistant coating, Journal of Nanoparticle Research, 2002, pp. 433-438, vol. 4, abstract.

Jin, et al., Nanoparticle-mediated drug delivery and gene therapy, Biotechnol. Prog, 2007, pp. 32-41, vol. 23, abstract.

Eck, et al., PEGylated gold nanoparticles conjugated to monoclonal F19 antibodies as targeted labeling agents for human panceatic carcinoma tissue, ACS Nano, 2008, pp. 2263-2272, vol. 2, No. 11, abstract.

Nafee, "Cationically-modified nanoparticles for the pulmonary delivery of the telomerase inhibitor 2'-O-Methyl RNA for the treatment of lung cancer," Dissertation zur Erlangung des Grades des Doktors der, Naturwissenschaftern der Naturwissenschaftilich-Technischen Fakul't III Chemie, Pharmazie, Bio-und Werstoffwissenschaften der Universit des Saarlandes, Jan. 7, 2009, title page.

Nazem, et al., Nanotechnology for Alzheimer's disease detection and treatment, Insciences J., 2011, pp. 169-193, vol. 1, No. 4, abstract.

Oliver, et al., Synthesis of pegylated immunonanoparticles, Pharmaceutical Research, 2002, pp. 1137-1143, vol. 19, No. 8, abstract.

Otsuka, et al., PEGylated nanoparticles for biological and pharmaceutical applications, Advanced Drug Deliveriy REviews, 2003, pp. 403-419, vol. 55, abstract.

Qi, et al. Redispersible hybrid nanopowders; cerium oxide nanoparticles complexes with Phosphonated-PEG oligomers, ACS Nano, 2008, pp. 879-888, vol. 2, No. 5, abstract.

Sokolov, et al., Real-time vital optical imaging of precancer using anti-epidermal growth factor receptor antibodies conjugated to gold nanoparticles, Cancer Res. 2003, vol. 63, title page only.

Suh, et al., Multifunctional nanosystems at the interface of physical and life sciences, Physicaplus, 2010, issue 13, abstract.

* cited by examiner

Ambient light

Ambient light + IR laser excitation

BIOCOMPATIBLE NANO RARE EARTH OXIDE UPCONVERTERS FOR IMAGING AND THERAPEUTICS

This application claims the benefit of priority to U.S. Provisional Application No. 61/081,903 filed on Jul. 18, 2008 and was funded in part by National Science Foundation Nanoscale Interdisciplinary Research Teams (NSF NIRT) (0708172 CBET) and National Institutes of Health (NIH) RO1 (1R01AG031529-01).

FIELD OF THE INVENTION

This invention relates to nanoparticles and, in particular, to methods and systems for up-converter tagged nanoparticles and up conversion nano cerias for site selective drug delivery and treatment of diseases.

BACKGROUND AND PRIOR ART

Understanding the complex spatio-temporal interplay of nanomaterials used as therapeutics at the cellular to the molecular level is required for designing nanoparticle based therapeutics and biomarkers for many diseases. To study these interactions, fluorescent labeling is commonly used for both in vivo cellular imaging and in vitro assay detection. Conventional fluorescence imaging involves single photon excitation of higher energy to emit lower energy light, a process known as down conversion. Organic dyes, metal and semiconductor nanoparticles are widely used as fluorophores to follow ligands into the cells and within tissue in animals as described in Michalet X, Pinaud F, Bentolila L, Tsay J, Doose S, Li J, Sundaresan G, Wu A, Gambhir S, Weiss S. Quantum Dots for Live Cells, in Vivo Imaging, and Diagnostics. Science 2005; 307, pp. 538-544. The fluorophores suffer from auto-fluorescence from biological tissues, photobleaching, low signal-to-noise ratio, potential damage to DNA and cell death as described in Green M, Howman E. Semiconductor quantum dots and free radical induced DNA nicking. Chem Commun 2005, pp. 121-123 and in Riegler J, Nann T. Application of luminescent nanocrystals as labels for biological molecules. Anal Bioanal Chem 2004, 379, pp. 913-919.

Up conversion phosphors (UCPs) capable of converting near infrared (NIR) radiation into shorter wavelengths through a multi-photon process, offers an alternative with minimal photo damage and auto-fluorescence due to the non-invasive nature of light as described in Auzel F. Upconversion and Anti-Stokes Processes with f and d Ions in Solids. Chem Rev 2004, pp. 139-173. Since up conversion occurs within the host crystal and is therefore less affected by the chemical and biological environments, and allows synthesis of materials without the loss of surface chemical reactivity.

All these favorable properties indicate that there is a real potential for the development of up conversion phosphors in the analysis of biological samples, especially for fluorescent imaging in vivo. Up conversion phosphors contain a sensitizer ion which absorbs the near infrared photons and transfers the absorbed energy sequentially to excite an emitter ion into a state which then emits in the visible. Lanthanide ions are particularly suitable candidates for up conversion processes because of their energy level structure providing many intermediate levels with favorable spacings and long-lived excited states. $Yb^{3+}$ ions have been widely used as sensitizer as $Yb^{3+}$ ions exhibit a relatively large absorption cross section in the near infrared region allowing excitation with laser diodes.

Metal fluorides, oxysulfides and phosphates are the matrices widely used to study the up conversion process and only a few reports are available with oxides. However, in order to have biocompatibility, a silica layer has been often coated on the surface of up conversion phosphors. Among the rare earth oxides, cerium oxide nanoparticles (CNPs) are shown to be biocompatible and exhibit regenerative antioxidant properties.

Earlier studies by co-inventors indicate that cerium oxide nanoparticles offer carbonic anhydrase inhibition, protection of primary cells from the detrimental effects of radiation therapy, prevention of retinal degeneration induced by intracellular peroxides, and neuroprotection to spinal cord neurons and have radical scavenging properties. By tailoring the surface potential or conjugating with targeting agents, specific uptake of cerium oxide nanoparticles in cells can be achieved. Although enhanced cellular uptake has been optimized based on surface characteristics, the mechanism of interaction, absorption and metabolism of these nanomaterials under in vivo condition is poorly understood.

The interaction of cerium oxide nanoparticles with cells and tissues needs to be well established for biomedical applications. Through real time imaging of cell-nanoparticle interactions it is possible to better understand the complex processes and conditions that facilitate or inhibit the uptake and release of materials into the cytosol or other intracellular targets. But, cerium oxide nanoparticles show weak emission characteristics in visible region, inhibiting the direct use of these materials for imaging purposes. One of the approaches to enhance the emission of cerium oxide nanoparticles is by doping with europium which has strong emission in the visible region. But, combining the non-toxic, biocompatible properties of cerium oxide nanoparticles with up conversion dopants would be a novel approach to optimize the emission properties. However, it is important to assess the interaction between the nanoparticles and cells since the biocompatibility and cellular uptake properties determine the therapeutic and imaging applications.

The present invention focuses on the formulation of co-doped cerium oxide nanoparticles with $Yb^{3+}$ sensitizer and mainly $Er^{3+}$ as an emitter. These co-doped, annealed cerium oxide nanoparticles will hereafter be referred to as up conversion nano ceria (UNC). In order to demonstrate the emission wavelength tunability, the emitter ion was changed to $Ho^{3+}$ or $Tm^{3+}$. The physical and optical properties of up conversion nano ceria and characteristics of these novel materials in various cells (A549, WI-38, HUVEC) were investigated by the co-inventors. In order to assess the antioxidant properties, catalase mimetic activity to catalyze the decomposition of hydrogen peroxide into water and oxygen was studied. The influence of nanoparticle interaction on the cell viability of normal lung fibroblasts (CCL-135) and cancerous cells (CRL-5803) were analyzed.

SUMMARY OF THE INVENTION

A primary objective of the invention is to provide methods, apparatus and systems for doping cerium oxide and other therapeutically valuable nanoparticles with rare earth ions either singly or in combinations so that infrared light is absorbed and visible light is emitted through the process of up conversion.

A secondary objective of the invention is to provide a novel type of therapeutic nanoparticle with rare earth doping to provide for up conversion emission for tracking and evaluating the functionality of the nanoparticles and further elucidation of ROS scavenging mechanism.

A third objective of the invention is to provide methods, apparatus and systems for using up converting rare earth nanoparticles to locate and estimate their presence in cells for finding, tracking and evaluating the therapeutic functionality of nanoparticles and other therapeutic agents in biological systems.

A first embodiment provides a method of doping a cerium oxide nanoparticle with one or more dopants to form co-doped up conversion nanoparticle ceria, at least one of the dopants absorbing infrared light and emitting visible light through the process of up conversion. The dopants are obtained from one or more nitrates selected from the group including of Yb, Er, Ho, Tm and Pr, such as co-doping Yb with one or more nitrates from the group consisting of Er, Ho, Tm and Pr, doping a cerium oxide nanoparticle with one of $Yb^{3+}$ and $Er^{3+}$, or adding one of $Er^+$, $Ho^{3+}$ and $Tm^{3+}$ to the $CeO_2$ nanoparticle. In an embodiment the up conversion nanoparticle ceria are Er, Yb doped $CeO_2$ particles. Applications include using the up converting nano ceria nanoparticles to locate cells using the up converting nano ceria nanoparticles for finding, tracking and evaluating therapeutic agents in biological systems.

Beyond Yb oxides, the embodiments also contemplate as up conversion sensitizer dopants metal oxides selected from the group including but not limited to La, Nd, Gd and Eu rare earth metal oxides.

As another embodiment, a cerium oxide nanoparticle is co-doped with a rare earth oxide selected from the group consisting of La, Nd, Gd and Eu with Yb sensitizer and Er as an emitter.

The cerium oxide nanoparticle can be co-doped with an up-converting material to form an up conversion nano ceria that absorbs infrared light and emits visible light through the process of up conversion including emitting one of a red, a green and a blue light.

Further objects and advantages of this invention will be apparent from the following detailed description of preferred embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Prior up-conversion patents include U.S. Pat. No. 5,089,860 issued to Deppe et al, on Feb. 18, 1992, U.S. Pat. Nos. 6,327,074 and 6,501,590 issued to Bass et al. respectively on Dec. 4, 2001 and Dec. 31, 2002, U.S. Pat. No. 6,654,161 issued to Bass et al. on Nov. 25, 2003, U.S. Pat. No. 6,844,387 issued to Bass et al. on Jan. 18, 2005, U.S. Pat. No. 7,075,707 issued to Rapaport et al. on Jul. 11, 2006 and U.S. Pat. No. 7,471,306 issued on Dec. 30, 2008 having a common inventor and assigned to the same assignee as the subject invention are incorporated herein by reference hereto.

U.S. patent application Ser. No. 12/365,971 filed on Feb. 5, 2008; Ser. Nos. 12/124,620 and 12/124,234 filed on May 21, 2008, Ser. No. 12/349,712 filed on Jan. 7, 2009, Ser. No. 12/365,971 filed on Feb. 5, 2009 and 61/180,475 filed on May 22, 2009 each having a common inventor and which are assigned to the same assignee as the subject invention, are also incorporated herein by reference hereto.

The present invention relates to the synthesis of rare earth co-doped cerium oxide nanoparticles having strong NIR-to-visible up conversion fluorescence. The tunability of emission wavelength was studied with respect to co-dopant chemistry on excitation with the wavelength of 975 nm. Cellular uptake of nanoparticles in A549, WI-38 and HUVEC cells was followed with NIR excitation and cytotoxicity of the particles were assessed by using MTT and LDH assay. Antioxidant catalase mimetic activity of nanoparticles was followed by the decomposition of hydrogen peroxide. Cell viability of normal lung fibroblasts and lung cancer cells with nanoparticle was investigated to ascertain the interaction of nanoparticle with normal and cancerous cells. The results from this study revealed that the biocompatible, co-doped cerium oxide nanoparticles exhibited strong up conversion properties which can be utilized for real time tracking of nanoparticles such as in cellular uptake as well as in biocatalytic activity, demonstrating the potential applications in cancer therapy.

The present invention focuses on the formulation of co-doped cerium oxide nanoparticles with $Yb^{3+}$ sensitizer and mainly $Er^{3+}$ as an emitter. These co-doped, annealed cerium oxide nanoparticles will hereafter be referred to as up conversion nano ceria (UNC). In order to demonstrate the emission wavelength tunability, the emitter chemistry was changed to $Ho^{3+}$ or $Tm^{3+}$. The physical and optical properties of up conversion nano ceria and characteristics of these novel materials in various cells including A549, WI-38, and HUVEC were investigated by the co-inventors. In order to assess the antioxidant properties, catalase mimetic activity to catalyze the decomposition of hydrogen peroxide into water and oxygen was studied. The influence of nanoparticle interaction on the cell viability of normal lung fibroblasts (CCL-135) and cancerous cells (CRL-5803) were analyzed.

Experimental Data:

Analytical grade nitrates of Ce, Yb, Er, Ho and Tm from Sigma-Aldrich Chemical Inc. were used for synthesis of up conversion nanophosphors. Ammonia solution (1N Alfa Aesar) was added to aqueous nitrate solutions of $Ce^{3+}$ (0.1 M), $Yb^{3+}$ (20%) and $Er^{3+}$ (2%) to maintain the pH above 10. The resultant precipitate was washed, annealed at 900° C. and filtered through 100 nm membrane filter, referred as up conversion nano ceria. A similar procedure was used to synthesize $CeO_2$:20% Yb, 2% Ho and $CeO_2$:20Yb %, 0.5% Tm.

The powders were characterized by X-ray diffraction (Rigaku) and high resolution transmission electron microscopy (Tecnai F30) to evaluate the structure and size. The optical absorption spectrum was recorded with Cary 500 Spectrophotometer. A diode laser emitting at 975 nm was used was used for the luminescence and time decay studies. Only up conversion nano cerias were used for imaging and therapeutic property assessment.

A549, WI-38, CRL-5803, and CCL-135 were obtained from American Type Culture Collection (Manassa, Va., USA) and Human Umbilical Vascular Endothelial Cells (HUVEC) cells were obtained from Lonza Walkersville, Inc. (Walkersville, Md., USA). A549, CRL-5803, and CCL-135 cells were cultured in Dulbecco's modification of Eagle's medium (DMEM) (Mediatech, Inc, Manassa, Va., USA) supplemented with 10% fetal bovine serum (FBS) (Equi-tech Bio, Kerrville, Tex., USA) and 100 IU $mL^{-1}$ penicillin (Mediatech, Inc, Manassa, Va., USA). WI-38 cells were cultured in Eagle's Minimum Essential Medium (EMEM) supplemented with 10% FBS and 100 IU $mL^{-1}$ penicillin. HUVEC cells were cultured in Endothelial Cell Medium (ECM) (Science-Cell, San Diego, Calif., USA) supplemented with 5% FBS and 100 IU $mL^{-1}$ penicillin. All cultures were maintained at 37° C. in a humidified incubator under a 5% atmosphere of $CO_2$.

Cells were cultured in 96-well culture dishes using appropriate media conditions and treated with up conversion nano cerias in varying concentrations; 0, 50, 250, 500, 750, 1000 µM and incubated for 24 h at 37° C. MTT dye (3-(4,5 dimethylthiazol-2-yl)-2,5-diphenyl tetrazolium bromide) (Amresco, Solon, Ohio, USA) was added to a final 1.2 mM concentration and cells were incubated another 4 hours at 37° C. To solubilize the dye, cells were lysed (10% SDS, 0.01 M HCl) and incubated overnight at 37° C. Absorbance was measured at 570 nm using a SpectraMax 190 spectrophotometer (Molecular Devices, Sunnyvale, Calif., USA). Cell proliferation was determined by dividing the absorbance of treated samples to untreated controls and reported as a percentage. Lactate dehydrogenase (LDH) release was measured in presence of up conversion nano ceria using Cytotoxicity Detection Kit$^{PLUS}$ (LDH) (Roche Diagnostics, Germany). In short, supernatants from each well was collected and spun to remove cell cellular debris. Freshly prepared reaction mixture was added, incubated for 15 min at RT protected from light. Stop solution was added and absorbance was measured at 490 nm. LDH release was determined as percentage of untreated control samples.

All samples for microscopy were prepared as follows. Cells were grown to approximately 60-70% confluence. After 24 hour treatment with various up conversion nano ceria concentrations, cells were washed 2 times in appropriate saline (A549 and WI-38, Dulbeccos's Phosphate Buffered Saline, (Mediatech, Inc, Manassa, Va., USA), HUVEC, Hepes Buffered Saline without Phenol Red, (Lonza Walkersville, Inc., Walkersville, Md., USA), trypsinized and transferred to glass coverslips. After a further 24 hour growth, cells were washed 2 times in appropriate saline, fixed in cold (20° C.) methanol for 10 min at RT then washed 2 times with sterile water.

All spectrophotometric data was collected using a 40 µL quartz cuvette with a 1 cm path length in a Hewlett-Packard diode array UV-visible 8453 spectrophotometer. Reactions were carried out in assay buffer containing 50 mM Tris, pH 7.5 and 1 mM diethylenetriaminepentacetic acid (DTPA) to chelate any possible adventitious metal. Hydrogen peroxide (Acros Organics) was added to start the reaction and samples were analyzed for a total of 600 seconds with a cycle time (time point) of 0.5 seconds at a wavelength of 240 nm. Up conversion nano ceria preparations were reconstituted in $H_2O$ to initial concentration of 10 µM and ultrasonicated for 45 min before use.

To evaluate the size of up conversion nano cerias, high resolution transmission electron microscopic (HRTEM) studies were carried out. In the as prepared condition size of the nanoparticle was found to be in the range of 7-10 nm. In the experiment, the size of the nanoparticle was between approximately 7 and approximately 10 nm while the mean crystallite size was calculated to be approximately 8.4 nm. Lattice parameter was found to be approximately 0.5423 nm in the as prepared condition and decreased to 0.5412 nm upon annealing. Cerium can exist in either +3 or +4 oxidation states. In the nanoscale the concentration of $Ce^3$ increases. As a result of higher ionic radii of $Ce^{3+}$ (0.1143 nm) than $Ce^{4+}$ (0.97 nm), the lattice parameter is larger than that of bulk ceria (0.541 nm). Further, trivalent Yb and Er dopant ions have higher ionic radii (0.0985 nm and 0.1004 nm, respectively) than that of $Ce^{4+}$. As a result prepared nanoparticles have higher lattice parameter than that of bulk ceria. On annealing $Ce^{3+}$ concentration decreases leading to a reduction in the lattice parameter.

Since the nanoparticle was in the form of a powder, a strip of dual sided transparent tape was placed on a glass slide and the particles were sprinkled on the exposed sticky side of the tape. This resulted in a sample that could be placed in the spectrophotometer so that its absorption spectrum could be measured. The absolute value of the absorption strength was not critical to the project but the absorption spectrum was and such samples enabled absorption spectra measurements. The emission spectra of co-doped cerium oxide nanoparticles were measured using the apparatus shown in FIG. 1. This procedure had been developed in prior research (A. Rapaport, J. Milliez, M. Bass, A. Cassanho, H. Jenssen, J. of Display Technology 2006, 2, 68).

Figure 1:
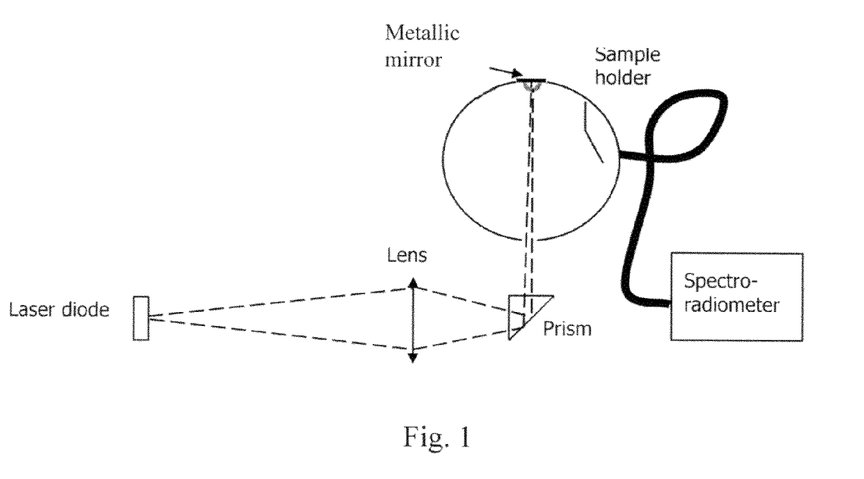
FIG. 1 is a block diagram of the experiment used to determine the emission spectra of the samples.

A diode laser emitting at 975 nm excited samples placed in the integrating sphere as indicated. The particles being studied were confined in a small cavity at the center of a clear cabochon. In FIG. 1, the metal mirror indicated in the block diagram was removed so that the green emission from a sample could be photographed. An integrating sphere and Instrument Systems CAS140B spectrometer enabled collecting the emitted light and measurement of its spectrum. For decay studies, a Spectra Physics MOPO laser generating pulses at approximately 975 nm of about 4 nsec duration at approximately 10 Hz pulse repetition frequency was used to excite the samples and enable measurement of the emission decay dynamics. The emitted light was directed through a 975 nm blocking filter to a fast detector (Hamamatsu PMT H6780-20 with sub 1 nsec rise time) which was connected to a Tektronix 2440 oscilloscope (FIG. 2b). The recorded decays were stored digitally and later analyzed with Origin software.

Equipment was set up for the experiment to detect the nanoparticles when viewed through the microscope. First up conversion nano cerias were placed on a microscope slide and, when excited by the 975 nm light from the diode laser, were seen to emit red light. Then the particles were placed in a cell culture and when exposed to 975 nm light could be detected and distinguished easily from other black spots in the field of view. The doped nanoparticles were those black spots that emitted red light when exposed to the diode laser light as shown in FIGS. 5a through 5f. The images were captured by a CCD camera when the excitation is on and the emitting nanoparticles were seen as the red emitting items in the displayed image. To protect an experimenter from inadvertently being exposed to 975 nm laser light, the beam path was placed in an enclosure and a filter that blocked 975 nm light was placed in the microscope optics before any light could reach either the eyepieces or the CCD camera.

FIG. 2 shows the characterization of up conversion nano cerias. FIG. 2a is a HRTEM micrographs showing up conversion nano cerias with a size range of approximately 20 to approximately 40 nm. The inset in FIG. 2a shows the SAED pattern from A to D corresponding to (111), (200), (220) and (311) planes. The HRTEM in FIG. 2b shows up conversion nano cerias having the primary particle size of approximately 20 nm. The interplanar distance corresponds to (111) plane of flurite structured ceria. The EDAX spectrum of the nanoparticle in FIG. 2c shows the presence of Ce, Yb, Er and O along with C and Cu which comes from TEM grid. In FIG. 2d, the X-ray diffraction pattern indicates the retention of fluorite structure of ceria even upon annealing (JCPDS card No. 81-0792).

Figure 2A:
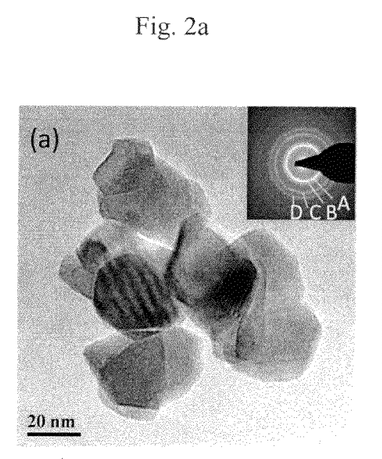
FIG. 2a is a HRTEM micrograph showing up conversion nano cerias with a size in the range between approximately 20 to approximately 40 nm. The inset shows the selected area electron diffraction pattern that shows the presence of fluorite structure.
Figure 2B:
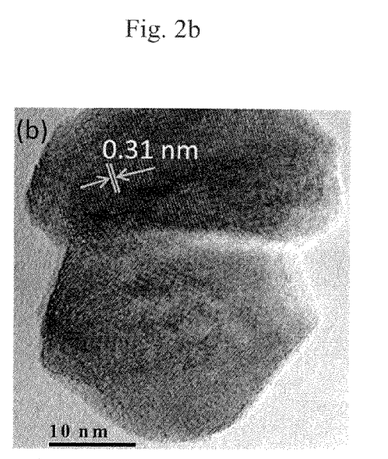
FIG. 2b is a HRTEM micrograph showing up conversion nano cerias with a size in the range of approximately 20 nm.
Figure 2C:
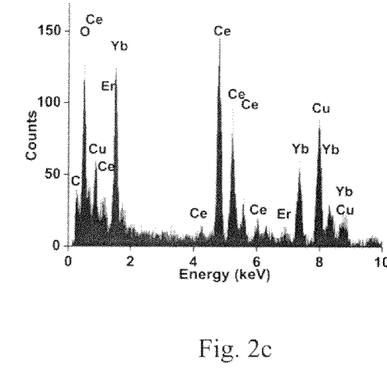
FIG. 2c shows an EDAX spectrum of the nano particle showing the presence of Ce, Yb, Er and O along with C and Cu.
Figure 2D:
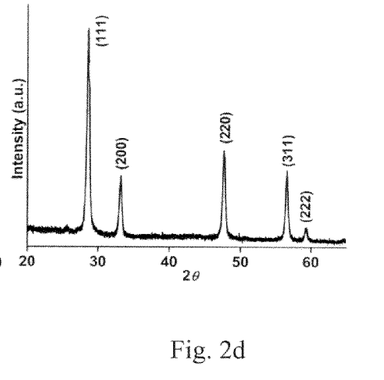
FIG. 2d shows an x-ray diffraction pattern that indicates the retention of fluorite structure of ceria.

On annealing, up conversion nano cerias have a primary particle size of about 20 nm along with a few particles in the size range of 40 nm, as a result interfusion to form larger particles due to annealing as shown in FIGS. 2a and 2b. Selected area electron diffraction (SAED) pattern shows the presence of fluorite structure as shown in the inset in FIG. 2a. Although the core particles still retained the nano size, the presence of few larger agglomerates is evident after filtration. From Energy dispersive analysis of X-rays as shown in FIG. 2c and X-ray diffraction shown in FIG. 2d, it can be concluded that $Yb^{3+}$ and $Er^{3+}$ were doped into the matrix of cerium oxide nanoparticles and hence no modification in diffraction pattern.

Previous studies of up conversion showed that fluoride crystals co-doped with $Yb^{3+}$ ions absorb light near 975 nm and then efficiently emit visible light depending on the co-dopant nature, Thus, the first step in optically characterizing up conversion nano cerias was to determine the $Yb^{3+}$ absorption spectrum in cerium oxide nanoparticles host. Details of the experimental set up used for optical property measurement were previously described.

Figure 3A:
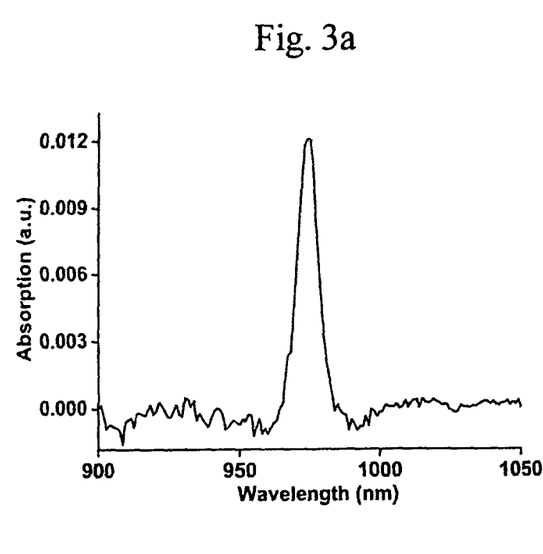
FIG. 3a shows the optical absorption spectrum of up conversion nano ceria.
Figure 3B:
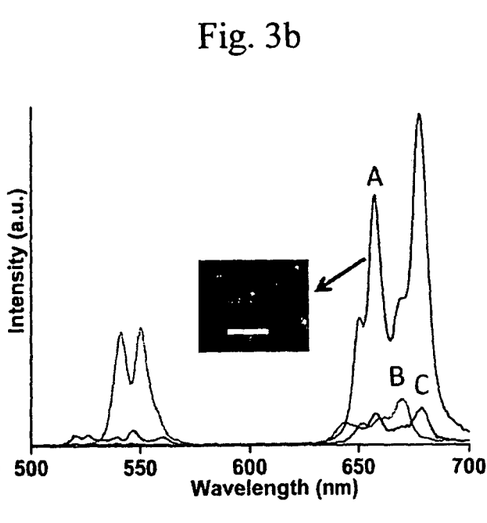
FIG. 3b shows the measured emission spectra of samples.
Figure 3C:
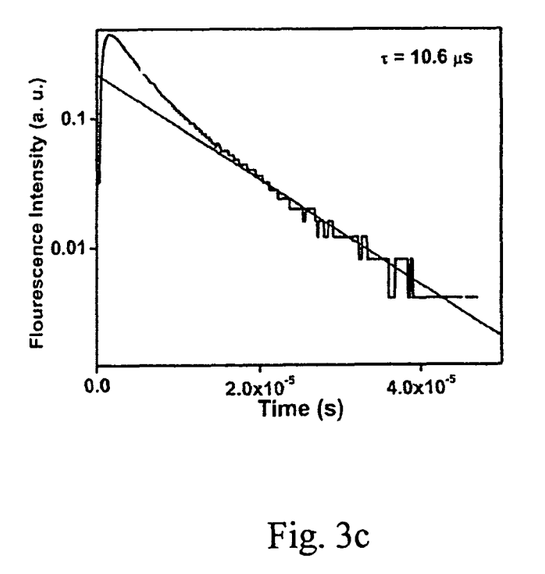
FIG. 3c shows the measured emission decay dynamics of the red light emitted from the up conversion nano ceria.

FIG. 2a is a graph showing the optical absorption spectrum of up converter nano ceria and FIG. 2b shows the measured emission spectra of samples of (A) up converter nano ceria, (B) $CeO_2$:20Yb %, 2% Ho and (C) $CeO_2$:20% Yb, 0.5% Tm. The transition $^4F_{9/2} \rightarrow ^4I_{15/2}$ lead to red emission in up converter nano ceria with a small amount of green light (around 540 nm $^4S_{3/2} \rightarrow ^4I_{15/2}$ transition) due to $Er^{3+}$. On co-doping with $Ho^{3+}$ green emission appears as a result of $^5F_4, ^5S_2 \rightarrow ^5I_8$ transition along with weak red light. $Tm^{3+}$ co-doping results in weak blue emission ($^1G_4 \rightarrow ^3H_6$) due to reduced probability for multi photon transition; inset demonstrates the red emission from up converter nano ceria observed from an optical microscope under NIR excitation. Scale bar in the inset corresponds to 10 μm. FIG. 3c is a graph showing the measured emission decay dynamics of the red light emitted from up converter nano ceria. The solid line is an exponential decay fit with decay time of 10.6 μsec. On near infra red excitation (975 nm), emission wavelengths can be tuned from red, green or blue on varying the co-dopant chemistry from $Er^{3+}$, $Ho^{3+}$ or $Tm^{3+}$, respectively.

From this data it is clear that the $Er^{3+}$ ions in cerium oxide nanoparticles emit principally in the red emission between approximately 640 and approximately 700 nm while $Ho^{3+}$ co-doping results in the green emission between approximately 530 and approximately 570 nm. Samples with $Tm^{3+}$ as the co-dopant were expected to emit blue light but the emission, if any, was too weak due to lower probability of multiphoton process. Up conversion nano ceria powders with $Yb^{3+}$ and $Er^{3+}$ co-dopants when excited by approximately 975 nm light from the diode laser could be easily seen to emit red light.

In earlier studies using fluoride hosts, the decay dynamics indicate a fluorescent lifetime of about 3 ms compared to 10.6 μs for up conversion nano ceria. A very short emission time observed in the present work indicates the presence of significant fluorescence quenching. Since oxide matrices have higher phonon energy than the fluorides this strong quenching is not surprising. In spite of quenching, the up conversion emission intensity is sufficient to utilize the water dispersible up conversion nano cerias as potential biomarkers. Thus, the emission color can be tuned from red, green or blue by varying the co-dopant from $Er^{3+}$, $Ho^{3+}$ and $Tm^{3+}$, respectively.

Recently several studies have shown that cerium oxide nanoparticles have potential for use as a biological antioxidant but opinion on toxicity of cerium oxide nanoparticles in cell culture models differs. As a result, although up conversion cerias have visible emission, the important step towards the biomedical application is to assess the toxicity in a wide range of concentrations. For the studies resulting in the present invention, the co-inventors chose several cell culture models including A549 adenocarcinoma cells, WI-38 human lung fibroblasts and Human Umbilical Vein Endothelial cells—HUVECs. The toxicity by the metabolic reduction of a tetrazolium dye (MTT) or by the release of lactate dehydrogenase (LDH) was assessed. By gauging cell viability using two independent methods, the co-inventors were confident that the cells are indeed viable under the experimental conditions.

Figure 4A:
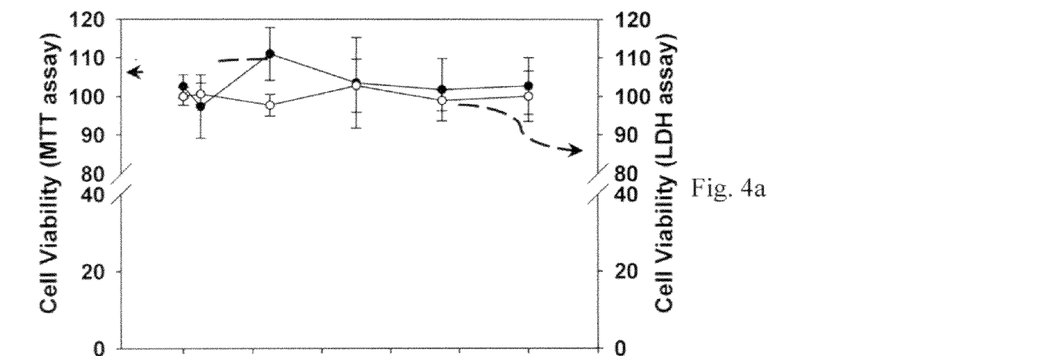
FIG. 4a shows up conversion nano cerias are not toxic in cell culture models of A549.
Figure 4B:
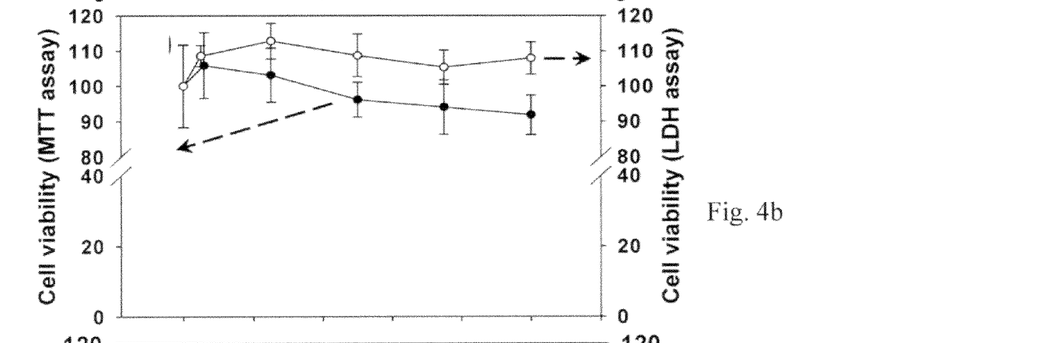
FIG. 4b shows up conversion nano cerias are not toxic in cell culture models of WI-38.
Figure 4C:
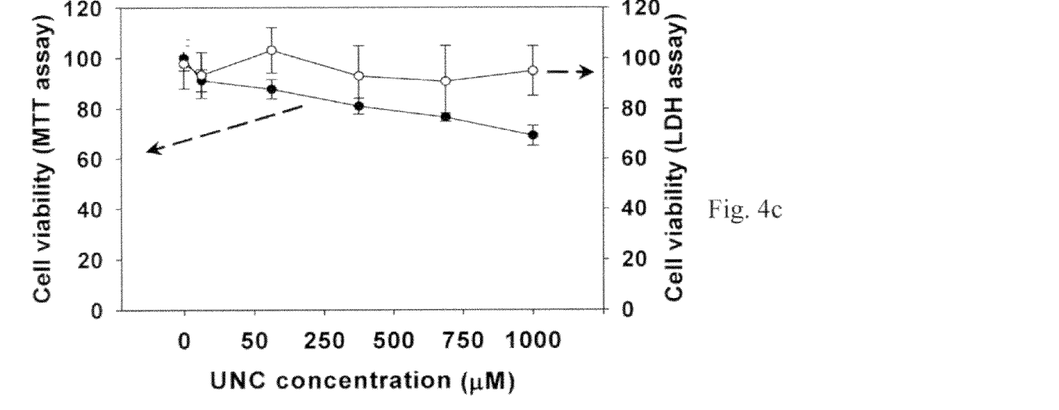
FIG. 4c shows up conversion nano cerias are not toxic in cell culture models of HUVEC.

When exposed to nanomolar and micromolar concentrations of materials, no significant toxicity was observed in A549 or WI-38 cells as shown in the graphs shown in FIG. 4a and FIG. 4b, respectively. Some toxicity was observed in HUVECs in a dose dependent manner when viability was determined by MTT assay, however no significant release of LDH occurred, suggesting the material caused a decrease in cellular metabolic rate without lysis of the cell membrane as shown in the graph of FIG. 4c.

Toxicity results indicate that up conversion nano ceriums are not toxic in cell culture studies, a key finding for their potential use in biomedical applications. In order to visualize up conversion nano ceriums in a biological model, the above mentioned model cell types were exposed in cultured monolayers to varying doses of up conversion nano ceriums, and observed a concentration-dependent increase in visible light emission when cells were excited using light at a wavelength of approximately 975 nm. An experimental set up was used to detect up conversion nano ceriums through the microscope. Particles were exposed to the culture models for 24 hours, cells were harvested by trypsin digest of extracellular matrix and then subsequently replated in culture dishes to form again a monolayer. Up converter nano cerias are absorbed by several human cells in culture.

Figure 5A:
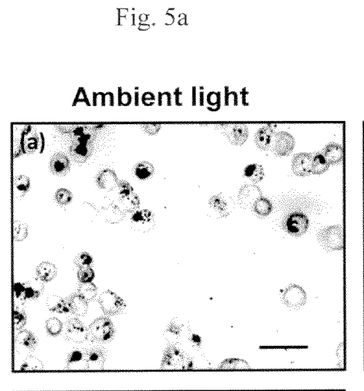
FIG. 5a shows up conversion nano ceria absorbed by human cells of A549 in a culture under ambient light.
Figure 5B:
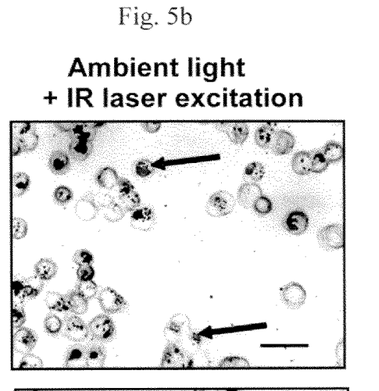
FIG. 5b shows up conversion nano ceria absorbed by human cells of A549 in a culture under ambient light plus infrared laser excitation.
Figure 5C:
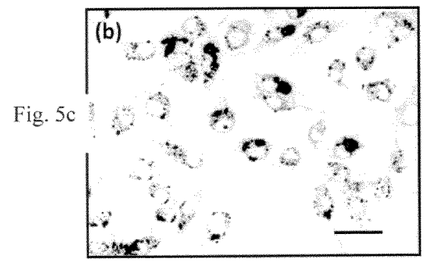
FIG. 5c shows up conversion nano ceria absorbed by human cells of HUVEC in a culture under ambient light.
Figure 5D:
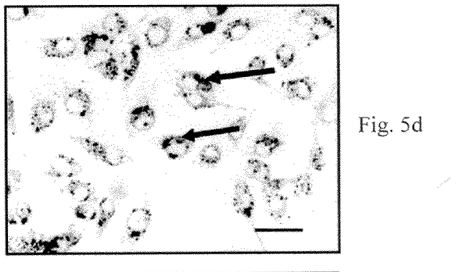
FIG. 5d shows up conversion nano ceria absorbed by human cells of HUVEC in a culture under ambient light plus infrared laser excitation.
Figure 5E:
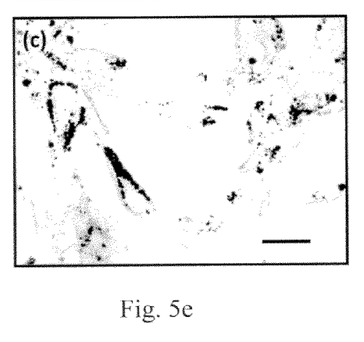
FIG. 5e shows up conversion nano ceria absorbed by human cells of WI-38 in a culture under ambient light.
Figure 5F:
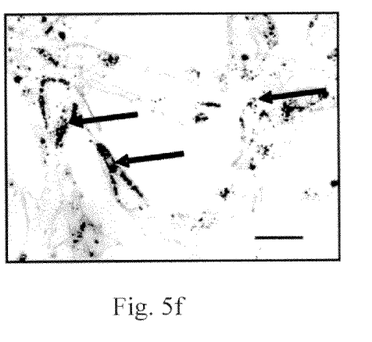
FIG. 5f shows up conversion nano ceria absorbed by human cells of WI-38 in a culture under ambient light plus infrared laser excitation

Cells of A549 are shown in FIGS. 5a and 5b, HUVEC are shown in FIGS. 5c and 5d and WI-38 are shown in FIGS. 5e and 5f, in the presence of ambient light in FIGS. 1a, 5c and 5f and near infrared excitation in FIGS. 5b, 5d and 5f with a wavelength of approximately 975 nm, approximately 4 ns pulse rate, approximately 10 Hz pulse repeat rate and a pump power of approximately 170 mW. Cells were incubated with cell monolayers for 16 hours in the presence of 100 µM up converter nano ceria. Cells were subsequently removed by trypsination from the monolayer to exclude loosely bound and excess up converter nano cerias, washed extensively in phosphate buffer solution, and replated on glass cover slips in 6-well tissue culture dishes. After 16 hours further incubation to allow for monolayer formation cells were fixed and observed by optical microscopy and the scale bar corresponds to 50 µm.

The image captured by the CCD camera when the excitation is on is shown in FIGS. 5b, 5d and 5f and the emitting nanoparticles can be seen as the red emitting items in the image. Arrows represent few of the particles which highlight under near infrared excitation. These images comprise only the replated cells, the results strongly suggest the up conversion nano cerias are intracellular and not simply loosely bound material to cells. The particles are somewhat larger, suggesting that agglomeration is likely to take place inside the cells after absorption although cellular uptake of agglomerated up conversion nano ceria is also possible. The aggregation of CNPs inside cells was shown in prior work by co-inventors using TEM studies depending on the surface potential of cells and nanoparticles.

Cellular uptake of smaller as well as larger (agglomerates) particles have also been reported. Transport of small particles primarily occurs by diffusion and endocytosis, while uptake of larger particles could be facilitated by sedimentation on the culture monolayer. Although the current optics used to image this particles have shown mostly agglomerated particles, still there may be the presence of finer particles which may be too weak to be observed with nanometer resolution using the experimental capabilities.

Figure 6A:
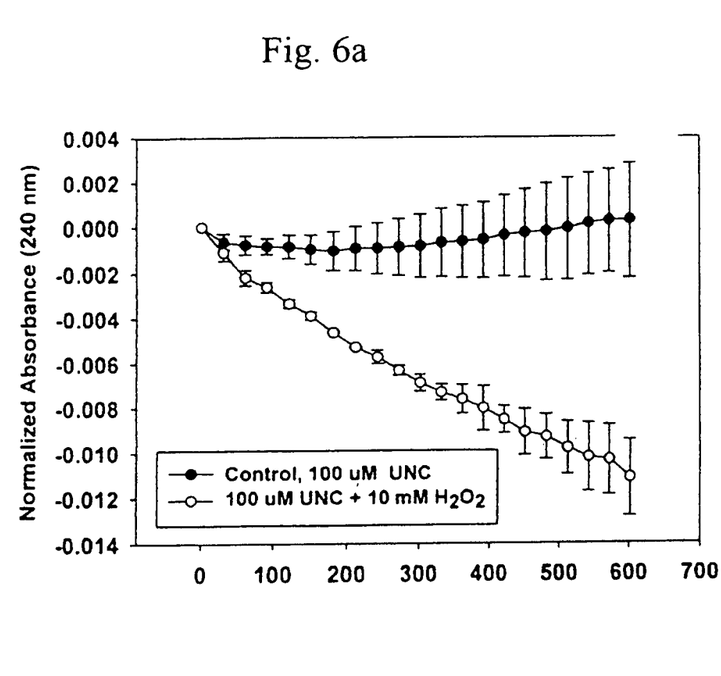
FIG. 6a is a graph showing the conversion of hydrogen peroxide to oxygen was followed by measuring decreases in hydrogen peroxide levels via ultraviolet absorption showing catalase mimetic activity.

Co-inventors have previously shown that cerium oxide nanoparticles can scavenge free radicals and mimic enzymatic antioxidants such as superoxide dismutase and catalase. Since up conversion nano cerias are biocompatible, biological catalytic activity was tested for potential biomedical applications. Catalse mimetic activity of up conversion nano cerias were followed by monitoring the peroxide levels using ultraviolet-visible spectrophotometry. FIG. 6a illustrates the role of up converter nano cerias in catalase mimetic activity and cancer treatment. FIG. 6a shows the conversion of hydrogen peroxide to oxygen was followed by measuring decreases in hydrogen peroxide levels via ultraviolet absorption (absorbance maximum at 240 nm). A representative experiment with at least three independent samples is shown, and the experiment was repeated at least two times on two preparations of cerium oxide nanoparticles. Data plotted represent the mean of at least three samples and the error plotted is the standard deviation of the mean.

The kinetics of these reactions was determined by measuring the decrease in absorbance of hydrogen peroxide at approximately 240 nm. In presence of 100 µM up conversion nano ceria, concentration of hydrogen peroxide reduced with time as shown in FIG. 6a. From this observation, it is evident that up conversion nano cerias are catalase mimetics, i.e. they convert hydrogen peroxide to molecular oxygen ($O_2$).

Although the mechanism of this activity is still under study, it could be due to radical scavenging properties of cerium oxide nanoparticles that have been recently reported by several groups. In order to investigate the effect of up conversion ceria on cancer cell proliferation in vitro, cell viability of cancerous lung cells (CRL-5803) and normal lungs fibroblasts (CCL-135) were tested with various nanoparticle concentrations. Cell viability of both of the cells was measured 72 hours post exposure to various concentrations of up conversion nano ceria. In the case of CRL-5803, proliferation of cancerous lung cells decreased by approximately 33.7% ($p<0.0001$) when exposed to approximately 100 nM of up conversion nano ceria.

To determine if this decrease in cell proliferation and viability was due to an increase in the activation of apoptosis, caspase-3/7 activity was measured 72 hours post up conversion nano ceria exposure. Caspase-3/7 activity increased by approximately 56.6% ($p=0.012$) when exposed to approximately 100 nM up conversion nano ceria. Under similar conditions, proliferation of normal lung fibroblasts increased by approximately 21.5% ($p=0.0178$) when exposed to approximately 100 nM up conversion nano ceria. To determine if this increase in cell viability was due to a decrease in the activation of apoptosis, caspase-3/7 activity was measured approximately 72 hours after up conversion nano ceria exposure. Caspase-3/7 activity did not significantly change in normal lung fibroblasts that were exposed to the various concentrations of up conversion nano ceria.

Recently co-inventors reported that under in vitro conditions, the cellular uptake of nanoparticles differs between a normal versus a tumor cell and can be attributed to the difference in intercellular activity, as well as cell structure. As a result of regenerative antioxidant properties of up conversion nano ceria, nanoparticles may reduce the proliferation of cancer cells. Nonetheless, recent studies on ZnO and $TiO_2$ show that these nanoparticles exert cancer killing activity through the reactive oxygen species generation or surface interaction with cells.

Recently, it has been reported that europium hydroxide nanorods show pro-angiogenic properties due to the formation of reactive oxygen species in a concentration dependent manner.

Based on the above facts, it is expected that up conversion nano cerias affect the equilibrium oxygen concentration of the cells in a cell specific reaction. In the case of cancerous cells it probably generates reactive oxygen species which annihilates the cancerous cells while enhancing the normal cell proliferation.

In conclusion, for biomedical application of up conversion nanoparticles, studies on toxicity are of considerable importance to understand the properties and potential applications. In this study conducted for the present invention, co-doped cerium oxide nanoparticles were synthesized by precipitation technique. Up conversion nano cerias that are biocompatible have shown to be a potential biomarker with antioxidant properties. Up conversion nano cerias interact in a cell specific manner preventing cancer cell proliferation while protecting normal cells, which can have a far reaching impact in future cancer research. With suitable surface targeting ligands, up conversion nano cerias could be used for site selective drug delivery for the treatment of diseases like cancer.

In summary, a first embodiment provides a method of doping a cerium oxide nanoparticle with one or more dopants to form co-doped up conversion nanoparticle ceria, at least one of the dopants absorbing infrared light and emitting visible light through the process of up conversion. The dopants are one or more nitrates selected from the group including of Yb, Er, Ho, Tm and Pr, such as co-doping Yb with one or more nitrates from the group consisting of Er, Ho, Tm and Pr, doping a cerium oxide nanoparticle with one of $Yb^{3+}$ and $Er^{3+}$, or adding one of $Er^{3+}$, $Ho^{3+}$ and $Tm^{3+}$ to the $CeO_2$ nanoparticle. in an embodiment the up conversion nanoparticle ceria are Er, Yb doped $CeO_2$ particles. Applications include using the up converting nano ceria nanoparticles to locate cells using the up converting nano ceria nanoparticles for finding, tracking and evaluating therapeutic agents in biological systems. The cerium oxide nanoparticle can be co-doped with an up-converting material to form an up conversion nano ceria that absorbs infrared light and emits visible light through the process of up conversion including emitting one of a red, a green and a blue light.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An up conversion nano ceria for site selective drug delivery and treatment of disease consisting essentially of:
    a water dispersible non toxic up conversion nano ceria consisting essentially of:
    a cerium oxide nanoparticle doped with Yb ions and at least one of an upconverting Ho, Tm, and Pr ion to form up conversion nanoceria emitters that absorb infrared light and emit a red, a green or a blue light through the process of up conversion.

2. A biocompatible non toxic up conversion nanoparticle consisting essentially of:
    a cerium oxide nanoparticle doped with $Yb^{3+}$ as a sensitizer and $Ho^{3+}$ as an emitter to form up conversion nano ceria that absorbs infrared light and emits visible light through the process of up conversion to emit red light as a biocompatible non toxic nano rare earth up conversion for imaging and therapeutics.

3. An up conversion nanoparticle consisting essentially of a doped nano ceria based up conversion material consisting essentially of:
    a ceria base material;
    a Yb sensitizer dopant ion doped into the ceria base material; and
    at least one emitter dopant ion selected from the group consisting of Ho, Tm and Pr emitter dopant ions, also doped into the ceria base material.

4. The nanoparticle of claim 3 wherein the doped nano ceria based up conversion material absorbs in the infrared wavelength range and emits in the visible wavelength range.

5. The nanoparticle of claim 4 wherein the nano ceria based up conversion material emits in the red portion of the visible wavelength range.

6. The nanoparticle of claim 4 wherein the nano ceria based up conversion material emits in the green portion of the visible wavelength range.

7. The nanoparticle of claim 4 wherein the nano ceria based up conversion material emits in the blue portion of the visible wavelength range.

8. An up conversion nanoparticle selected from the group consisting of CeO2:20%Yb, 2% Ho and CeO2:20%Yb, 0.5% Tm.

9. The up conversion nanoparticle of claim 3 wherein a size of the nanoparticle is from about 7 to about 10 nanometers.

10. The up conversion nanoparticle of claim 3 wherein a lattice parameter of the nanoparticle is from 0.5412 to 0.5423.

\* \* \* \* \*